United States Patent
Sahadevan

Patent Number: 5,842,987
Date of Patent: Dec. 1, 1998

[54] SIMULATED PATIENT SETUP FOR MEDICAL IMAGING WITH INCREASED PATIENT THROUGHPUT

[76] Inventor: Velayudhan Sahadevan, 200 Granville Ave., Beckley, W. Va. 25801

[21] Appl. No.: 858,963

[22] Filed: May 20, 1997

[51] Int. Cl.$^6$ ........................................................ A61B 5/05
[52] U.S. Cl. .................................. 600/407; 5/601; 5/611; 378/209
[58] Field of Search ............................... 324/318; 5/611, 5/601; 600/407, 410; 128/898; 378/65, 204, 209

[56] References Cited

U.S. PATENT DOCUMENTS

| | | | |
|---|---|---|---|
| 4,671,256 | 6/1987 | Lemelson | 128/1.1 |
| 4,791,934 | 12/1988 | Brunnett | 128/653 |
| 5,490,297 | 2/1996 | Bradcovich et al. | 5/601 |
| 5,490,513 | 2/1996 | Damadian et al. | 128/653.2 |
| 5,499,415 | 3/1996 | McKenna | 5/601 |
| 5,525,905 | 6/1996 | Mohapatra et al. | 324/318 |
| 5,537,452 | 7/1996 | Shephard et al. | 378/65 |
| 5,586,262 | 12/1996 | Komatsu et al. | 395/200.02 |
| 5,748,700 | 5/1998 | Shephard et al. | 378/65 |

Primary Examiner—Marvin M. Lateef
Assistant Examiner—Eleni Mantis Mercader
Attorney, Agent, or Firm—Steptoe & Johnson

[57] ABSTRACT

A preliminary simulated patient setup is done with a x-ray unit (14) or an ultrasound unit (16) with patient on a flat table top insert (68) on preliminary imaging tables (12) in preliminary imaging support rooms (10). Patient is transported from tables to table by sliding the flat table top insert (68) on these tables' cradle. If surgery is to be done, before or after surgery, patient is transferred to flat table top insert (68). Multiple preliminary imaging tables (12) are connected to patient transport room (26). It also connects to CT or MRI imaging room (32). A patient transport table (28), in patient transport room (26) makes connection with preliminary imaging tables (12), a mobile surgical table (22) and CT or MRI-table (36). After imaging, patient is unloaded to a patient unloading room (66). For use of a single CT or MRI for CT or MRI combined radiation therapy, patient is transported from CT or MRI scanning table (36) to patient handling table on rail (40) on rails (42) in accelerators' anteroom (38) and to accelerators' table (48) in accelerator room (44). Delivery of a required radiation dose to the CT or MRI verified treatment field generally takes only about a minute. With this system configuration, a continuous flow of patients can be imaged and or treated with a single CT or MRI (FIG. 1). For still further increased patient throughput, more than one CT or MRI and accelerator is used as in FIG. 5 and 6.

18 Claims, 5 Drawing Sheets

SIMULATED PATIENT SETUP FOR MEDICAL IMAGING WITH INCREASED PATIENT THROUGHPUT

CROSS-REFERENCES TO RELATED APPLICATIONS

This patent is based upon an application, which is a continuation-in-part of my copending U.S. application Ser. No. 08/712,623, filed 1996 Sep. 11 and PCT/US96/14143, filed 1996 Sep. 12.

BACKGROUND

1. Field of Invention

This invention relates to medical imaging, particularly to simulated patient setup for medical imaging with increased patient throughput.

2. Description of Prior Art

Heretofore medical imaging by computed tomography (CT) or magnetic resonance imaging (MRI) requires lengthy patient setup for the scan on a patient-handling table. It consumes more time than the actual completion of a scan protocol by the CT or MRI elements in a gantry. The gantry is idle during the lengthy period of the patient setup on a CT or MRI table. Therefore, the present CT and MRI can process only a few patients a day. In hospitals and clinics, multiple costly CT and MRI scanners are installed to handle the larger volume of patients. The limited number of patients that can be imaged with a single CT or MRI a day makes them quite inefficient for cost containment.

The recent developments in CT and MRI scanning technologies, particularly that for CT scans allows faster completion of a scan protocol. With a scan time of one second and inter-scan delay of a second, about twenty to thirty imaging of a desired anatomical site can be completed in about 75 seconds by a modern CT scanner. Usually, about 30 minutes are taken for the patient setup on a scanning table and after the scanning, for the patient unloading from the scanning table and the scanning room. This allows only about 20 patients scanning during an 8-hour work period of a day. In the usual clinical settings however, fewer than 20 patients can be scanned a day.

In general, for CT or MRI procedure, patient is brought into the imaging room and loaded onto a scanning table. The desired anatomical site selection for scanning is made with the patient on the scanning table. After the scanning patient is unloaded from this table and leaves the imaging room through the same entrance and exit door as the patient was brought in.

No prior thoughts were given on how to reduce the patient handling time in a CT or MRI imaging room. A reduction of the time taken for patient processing in the imaging room would enhance the utilization of CT or MRI scanners. As of now, emphases were on technological advancement for faster scanning. Most time consuming patient processing for CT or MRI procedure still remains as the same as it was when they were introduced long time ago.

In patent pending applications U.S. Ser. No. 08/712,623 and PCT/US96/14143 by this applicant, multiple CT or MRI are used for the combined imaging and radiation therapy of cancer. The cost-efficiency of this system can be further improved by reducing the number of required scanners.

For breast scanning, Damodian and Votruba, U.S. Pat. No. 5,490,513, 1996, describes additional patient handling capability at the primary magnetic field. If a multiple patient mode MRI scanner is built, it will increase the patient throughput. The possible method of multiple patient MRI breasts scanning cannot be generalized for scanning of the whole chest, abdomen and pelvis.

Multiple patient heads scanning with this system is theoretically described. The scan volume required in the primary magnet for the theorized head scanning will be much lesser than those required for scanning of the entire chest, abdomen and pelvic regions. This will require a large scan volume in the primary magnet.

A special iron core magnet with two plates connected to each other by vertical interconnecting parallel vertical support columns is described. It is to provide a large imaging volume to accommodate four or more patients' chest, abdomen or pelvic regions. This will add significant expense to this system.

The described simultaneous or sequential head scanning of two patents with fiducial markers to separate the image data needs to be further processed for separation of images of each of the patients and subsequent orientation for diagnostic interpretation. The careful separation, reorientation and subsequent diagnostic interpretation cause loss of time. It reduces the efficiency of this system.

There are also concerns for the safe separation and interpretation of each intended patient's data so that a particular patient's data will not be misinterpreted, as another patient's data. In simultaneous processing of spatially encoded imaging data from multiple patients scanning, an individual image will contain imaging data from multiple patients. Additional means are added to scan data collection system to separate each patient's scanned data. Here again the safety and costs are of important concerns. Time is also lost by these complex image processing. This makes it less efficient.

Modification and addition of single or some dual mode radio frequency antennas to cover larger imaging volume to scan chest, abdomen and pelvis are another complexity of this system and its added expense.

The MRI with multiple patients handling tables in MRI room is difficult to adapt for the development of a combined cost efficient MRI and radiation therapy system. To use the system as described by Damodian and Vortruba U.S. Pat. No. 5,490,513, 1996, for combined MRI and radiation therapy, four or more separate medical accelerators, one at each end of a scanning table facing the primary magnet's aperture is required. It is not practical. It is also very costly and inefficient.

OBJECTS AND ADVANTAGES

Accordingly, several objects and advantages of the invention are to provide a system of preliminary imaged patient setup on scanning table for CT or MRI which obviates the disadvantages of the prior patient handling in imaging room, specifically which reduces the patient handling time in the CT or MRI room and thereby increases the patient throughput by a CT or MRI.

It is a further object of the invention to take full advantage of the modern CT or MRI scanners' faster scan protocol processing for the increased patient throughput by a CT or MRI.

It is yet a further object of the invention to provide a single CT or MRI with its increased patient throughput to eliminate the multiple CT or MRI used in the parent patent pending applications U.S. Ser. No. 08/712,623 and PCT/US96/14143 for cost efficient medical imaging and radiation therapy with on-line isodose and port verification.

It is yet a further object of the invention to use a MRI unit with a single patient-handling table in association with a patient transport system to increase its patient throughput and cost-efficiency.

It is still another object of the invention to eliminate the direct loading and unloading of a patient to and from a CT or MRI scanning table by loading the patient on it indirectly after the preliminary patient setup and imaging in a preliminary imaging room.

It is another object of the invention to provide pre imaging rooms and a surgical room connected with a patient transport room for transfer of patient to CT or MRI room.

It is still another object of the invention to equip the preliminary imaging rooms with a preliminary imaging device such as a diagnostic x-ray or a 3-D ultrasound unit and a preliminary imaging table for the preliminary patients' setup.

It is another object of the invention to provide a flat table top insert on top of the preliminary imaging table for patient setup on it and transport of the patient in preliminary imaged position by moving the flat table top insert with the patient to the patient transport table and to the CT or MRI scanning table.

It is a further object of this invention to provide a patient transport room with a rotating patient handling table for patient transport from preliminary imaging or surgical room to CT or MRI scanning table.

It is a further object of the invention to provide a patient unloading.

Still, further objects and advantages will become apparent from a consideration of the ensuing description and accompanying drawings.

BRIEF DESCRIPTION OF THE DRAWINGS

REFERENCE NUMERALS 10 preliminary imaging support rooms
12 preliminary imaging table
14 x-ray unit
16 ultrasound unit
18 ultrasound unit's computer
20 surgical room
22 mobile surgical table
24 surgical table's rail
26 patient transport room
28 patient transport table
30 circular rail
32 final imaging room
34 final imaging device with its gantry
36 CT or MRI scanning tables
38 accelerator's ante-room
40 patient-handling table on rail
42 rail
44 accelerator room
46 accelerator
48 accelerator table
50 conveyer table on wheel
52 sliding doors
54 entrance and exit doors
56 gantry's front entrance
58 gantry's back exit
60 final imaging room's exit door
62 connecting door of accelerator's anteroom and accelerator room
64 accelerator room's intermediate wall's door
66 patient unloading room
68 flat tabletop insert
70 cradle
72 intermediate support
74 base assembly
76 grooves
78 rollers
82 CT or MRI scanning table's cradle
84 grooves of CT or MRI cradle
86 CT or MRI table's intermediate support
88 CT or MRI table's base assembly
90 break
94 dressing room
96 concrete wall

SUMMARY

A system for simulated patient setup for increased patient throughput by a single CT and MRI for medical imaging and a single CT or MRI combined with an accelerator for combined CT or MRI imaging and radiation therapy.

PREFERRED EMBODIMENT

Figure 1:
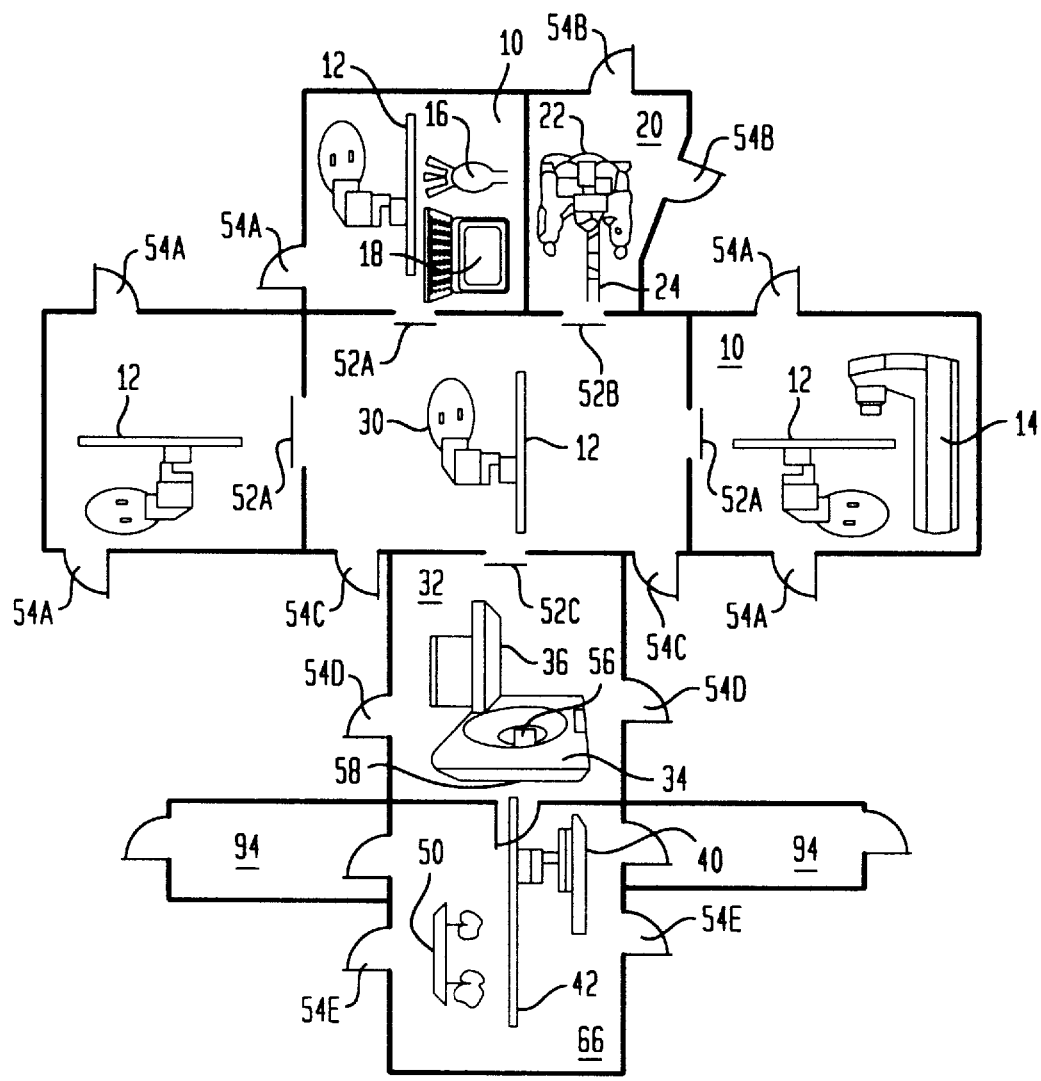
FIG. 1 is a perspective view of the invention for diagnostic imaging with increased patient throughput by a single CT or MRI.
Figure 3:
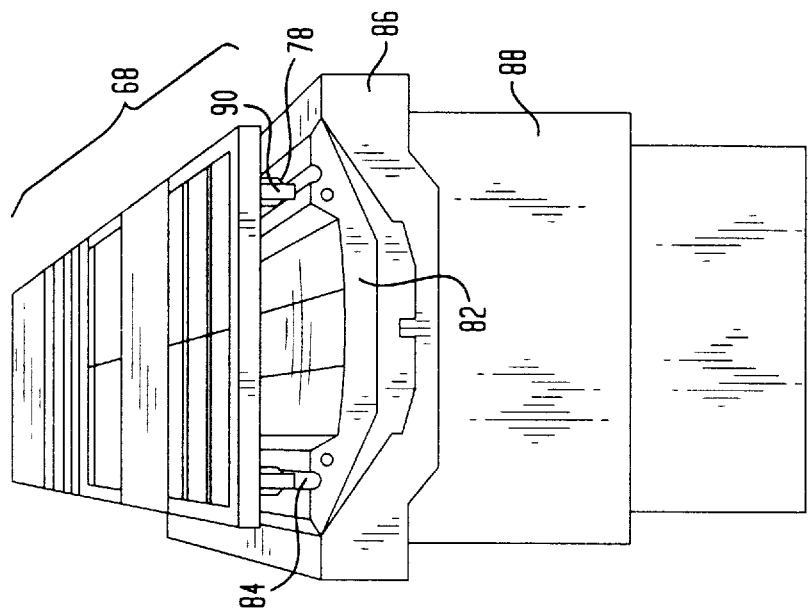
FIG. 3 shows the longitudinal view of the patient-handling table for CT or MRI in imaging room.
Figure 2:
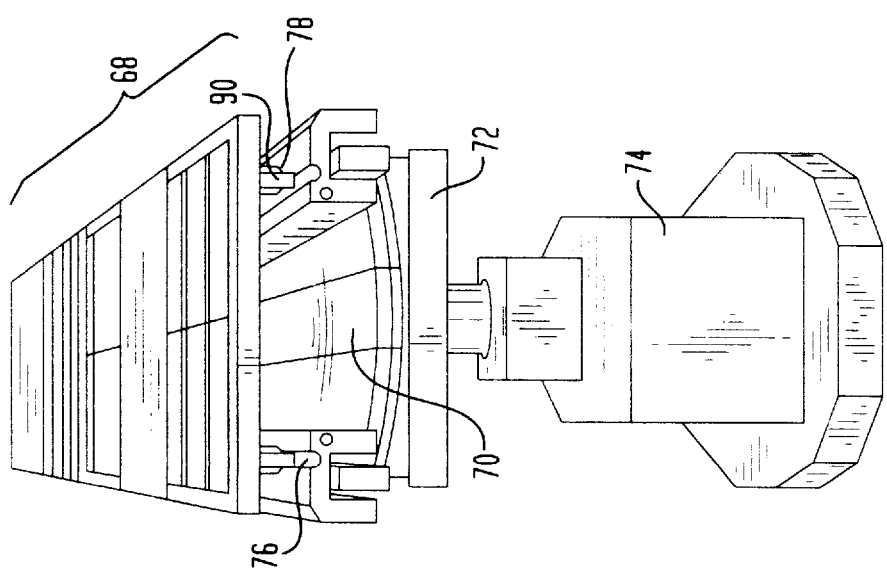
FIG. 2 is an overall longitudinal view of the preliminary imaging table, patient transport table, and patient handling table on rail and the accelerator table.

Description–FIGS. 1 to 3

FIG. 1. is an overall perspective view of the invention for diagnostic imaging with increased patient throughput by a single CT or MRI. It shows a plurality of preliminary imaging support rooms 10. It is equipped with a preliminary imaging table 12, a x-ray unit 14, an ultrasound unit 16, and an ultrasound unit's computer 18. A surgical room 20 is equipped with a mobile surgical table 22, on surgical table's rail 24. A patient transport room 26 contains a patient transport table 28, on circular rail 30. A final imaging room 32 is equipped with a final imaging device with its gantry 34, and a CT or MRI scanning table 36. A patient unloading room 66 is furnished with a patient handling table on rail 40, and a conveyer table on wheel 50. Patient unloading room 50 is attached to a dressing rooms 94.

In accordance with the invention, preliminary imaging support rooms 10, with x-ray unit 14, or ultrasound unit 16, and surgical room 20 are connected to patient transport room 26, with patient transport table 28. This patient transport table 28 is attached to circular rails 30. Sliding doors 52 A, and 52 B connect preliminary imaging support rooms 10, and surgical room 20, to patient transport room 26. Sliding door 52 C connects patient transport room 26, to final imaging room 32. Entrance and exit doors 54 A, 54 B, 54 C, 54 D, 54 E, are attached to preliminary imaging support rooms 10, surgical room 20, patient transport room 26, final imaging room 32, and to patient unloading room 66. The mobile surgical table 22 is attached to surgical tables' rails 24, on the floor. It leads to patient transport room 26. Gantry s' front entrance 56, faces CT or MRI scanning table 36, and gantry's back exit 58, faces final imaging room's exit door 60, which opens to patient unloading room 66. Patient handling table on rail 40 is attached to its rail 40 in patient unloading room 66. Dressing rooms 94 are attached to patient unloading room 66, through entrance and exit door 54 E.

FIG. 2 illustrates the longitudinal view of the patient handling table in preliminary imaging support rooms 10, in patient transport room 26, in accelerators' anteroom 38, in patient unloading room 66 and in accelerator room 44. They are equipped with a cradle 70, an intermediate support 72, and a base assembly 74. Cradle 70 is fitted with grooves 76. A flat tabletop insert 68 is rolled over grooves 76, of cradle 70. Rollers 78 and breaks 90 are attached to the undersurface of flat tabletop insert 68.

FIG. 3 shows the longitudinal view of CT or MRI scanning table 36. It is equipped with a CT or MRI scanning table's cradle 82, a CT or MRI table's intermediate support 86, and a CT or MRI table's base assembly 88. Cradle 82 is fitted with grooves 84. A flat tabletop insert 68 is rolled over grooves 84, of cradle 82. Rollers 78 and breaks 90 are attached to the undersurface of flat tabletop insert 68.

Operation–FIGS. 1 to 3

FIG. 1 is a perspective view of the invention for diagnostic imaging with increased patient throughput by a single CT or MRI.

The patient is brought to preliminary imaging support room 10, through entrance and exit door 54 A. Flat table top insert 68, is placed on top of preliminary imaging table 12. Patient is loaded onto flat tabletop insert 68. The desired anatomic region is defined with the aid of preliminary imaging x-ray unit 14, or preliminary imaging ultrasound unit 16, with ultrasound units' computer 18, for image processing. In case when preliminary imaging support rooms 10, is not equipped with a preliminary imaging x-ray unit 14, or preliminary imaging ultrasound unit 16, the desired anatomic site is approximated at this phase of the patient setup on preliminary imaging table 12. The patient whose setup for preliminary imaging is completed is moved onto patient transport table 28, in patient transport room 26, by sliding and rolling flat tabletop insert 68, with the patient on it on grooves on these tables. It allows the transport of the patient from preliminary imaging table 12, to patient transport table 28, without any changes in patients' positioning that was verified with the aid of the x-ray unit 14, or ultrasound unit 16, in preliminary imaging support room 10.

A patient for surgery combined CT or MRI imaging is placed on mobile surgical table 22, in surgical room 20, for surgery. Mobile surgical table 22, moves on surgical table's rails 24, for patients' transport. After or before surgery, the patient is transferred to flat tabletop insert 68. The flat table top insert 68, with the patient is transferred to patient transport table 28, in patient transport room 26 by sliding and rolling the flat table top insert 68 on grooves 76 of the patient transport table 28.

Patient transport table 28, on circular rail 30 is rotated toward preliminary imaging table 12, in preliminary imaging support rooms 10, or toward mobile surgical table 22, in surgical suite 20. The table ends are brought together through sliding doors 52 A or 52 B, for transfer of a patient from preliminary imaging table 12, or mobile surgical table 22, to patient transport table 28. Patient transport table 28 is made to rotate on circular rail 30, on the floor of patient transport room 26. After the patient's transfer to patient transport table 28, it is rotated toward final imaging room 32, with CT or MRI scanning table 36. Both table ends are brought together through imaging room's sliding door 52 C, for patients' transfer from patient transport table 28, to CT or MRI scanning table 36.

A patient on CT or MRI table 36 is advanced forward for scanning through gantry's front entrance 56. After the scanning, cradle 70, is advanced toward patient unloading room 66, through gantries' back exit 58, and final imaging room's exit door 60. Flat tabletop insert 68, with the patient is transferred to patient handling table on rail 40, in patient unloading room 66. It can be moved forward or backward on its rails 42, on the floor. The patient is unloaded from this table and the patient exits from patient unloading room 66, through its entrance and exit doors 54, to dressing rooms 94. Entry and exit to preliminary imaging support room 10, surgical room 20, patient transport room 26, final imaging room 32, and patient unloading room 66, are facilitated through their respective entrance and exit doors 54 A, 54 B, 54 C, 54 D, and 54 E.

The patient remains on flat tabletop insert 68, in an identical position throughout the entire course of patient transport. The simulated positioning of the patient is maintained as identical during the transfer of the patient from one table to another. After the completion of CT or MRI scanning, the patient is removed from flat tabletop insert 68. It is then placed on conveyer table on wheel 50, to be transported to the preliminary imaging support rooms 10, or to surgical suite 20, for its reuse for the next patient's setup and transport for imaging.

FIG. 2 is an overall longitudinal view of the preliminary imaging table, patient transport table, and patient handling table on rail and the accelerator table. Flat tabletop insert 68, can be rolled over grooves 76, of cradle 70, using its rollers 78. Cradle 70, can be advanced forward and backward on intermediate support 72. Intermediate support 72, and the cradle 70, are placed onto the base assembly 74.

Flat tabletop insert 68 is brought into preliminary imaging side rooms 10, and placed on top of cradle 70. Its rollers 78 is aligned with grooves 84, on cradle 70, and it is fixed on to cradle 70, by latching its brake's 90, onto grooves 76. The patient is then placed onto flat tabletop insert 68, on preliminary imaging table 12, for preliminary imaging and subsequent transport for CT or MRI imaging.

In case of surgery is to be associated with CT or MRI imaging, before or after surgery, the patient is transferred to flat tabletop insert 68. Desired patient positioning is established. The flat tabletop insert 68, with the patient is advanced to patient transport table 28, in patient transport room 26.

FIG. 3 illustrates the longitudinal view of CT or MRI scanning table 36. Flat tabletop insert 68, with its rollers 78, can be moved on CT cradle's 82, grooves 84. Flat tabletop insert 68, with patient is rolled over to CT or MRI scanning table 36. The patient is advanced toward gantries' front entrance 56, for patients' setup for scanning. After the scanning, flat tabletop insert 68, with the patient is moved toward the patient handling table on rail 40, in patient unloading room 66, through gantries' back exit 58. Flat tabletop insert 68, with the patient is transferred to patient-handling table on rail 40, by rolling flat table top insert 68, over the groove's 76, of patient handling table on rail 40. Cradle 82 is supported by intermediate support 86. Base assembly 88, holds CT or MRI scanning table 36, onto the floor.

Figure 4:
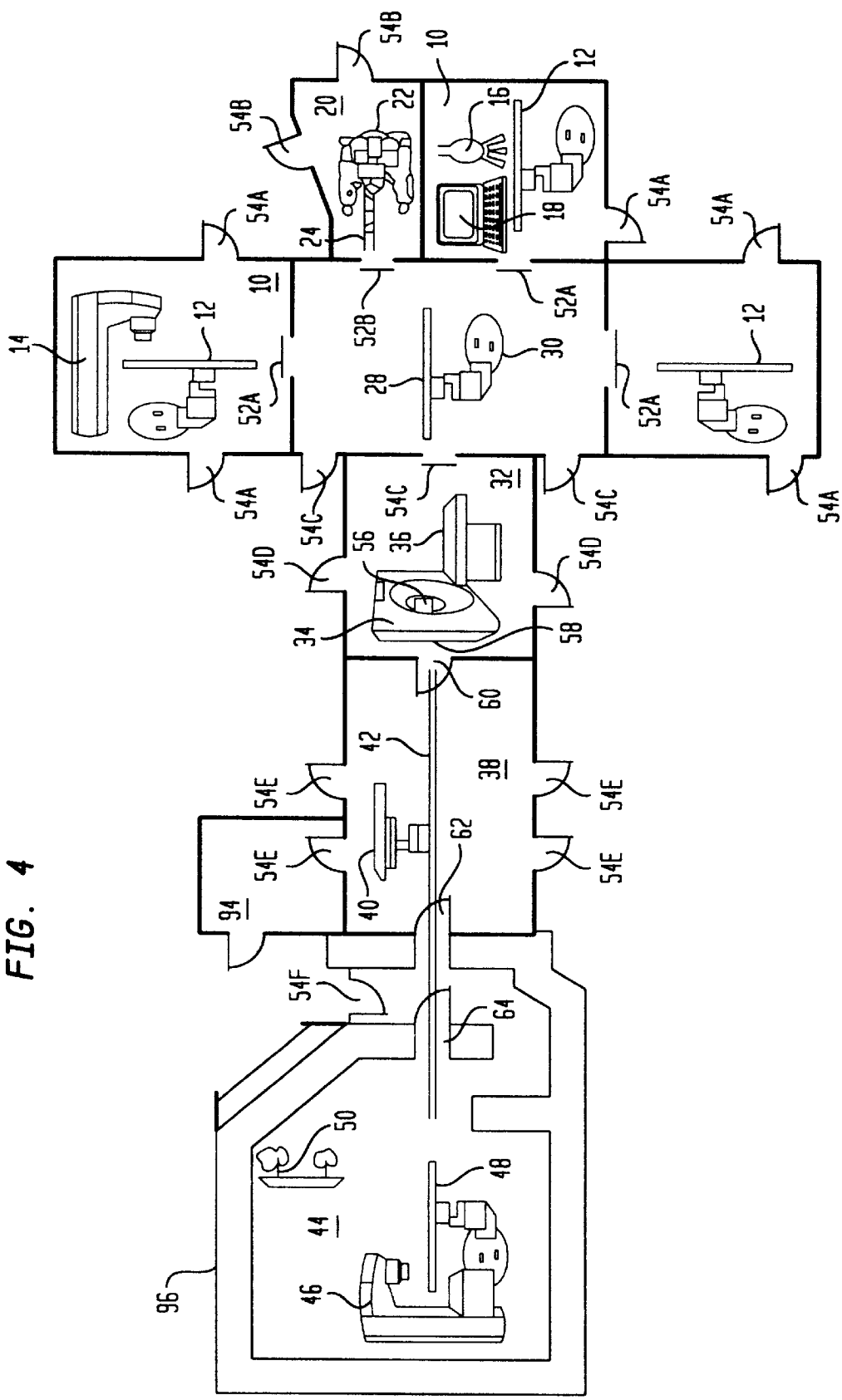
FIG. 4 is an overall perspective view of the combined medical imaging a radiation therapy.
Figure 5:
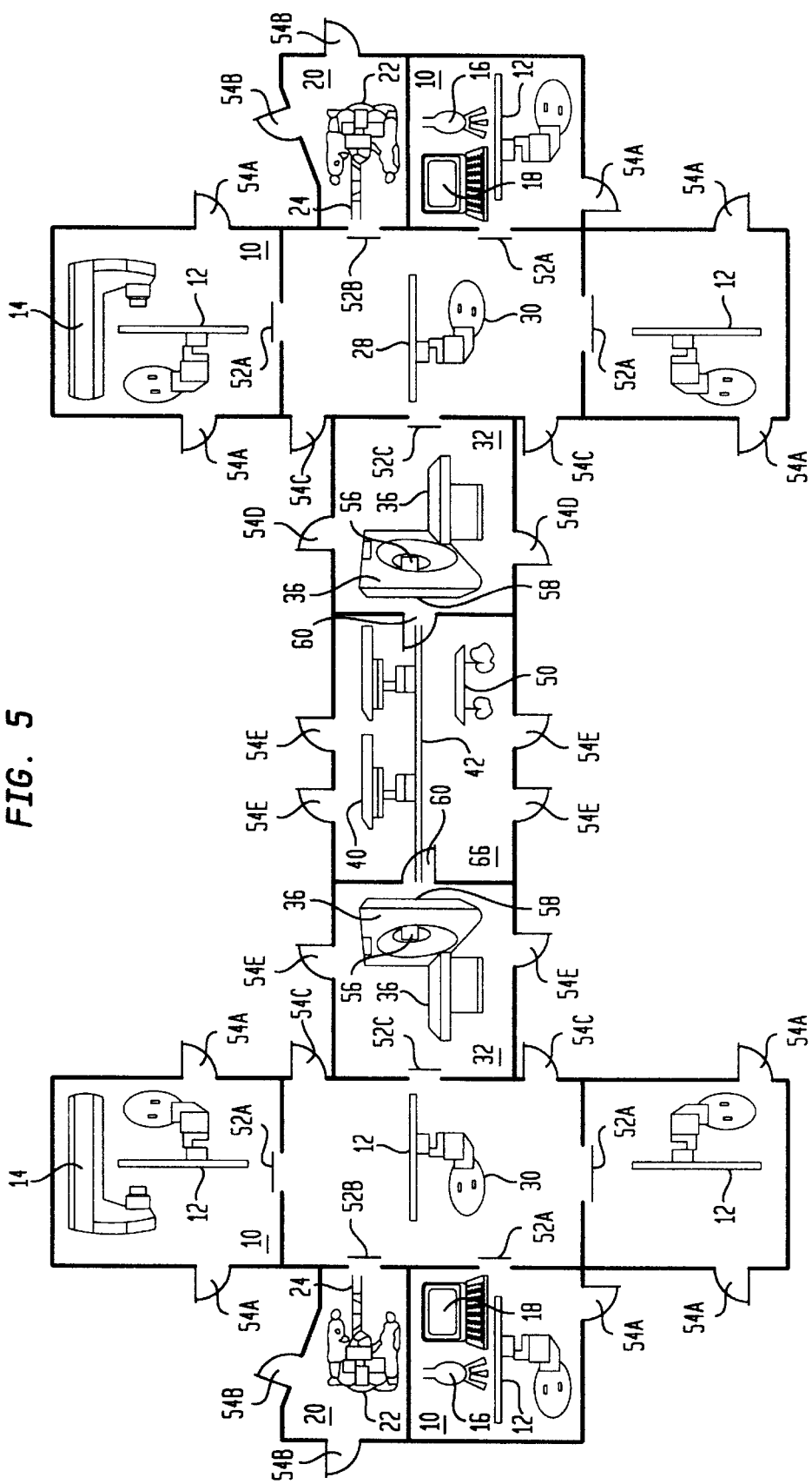
FIG. 5 shows two diagnostic imaging units.
Figure 6:
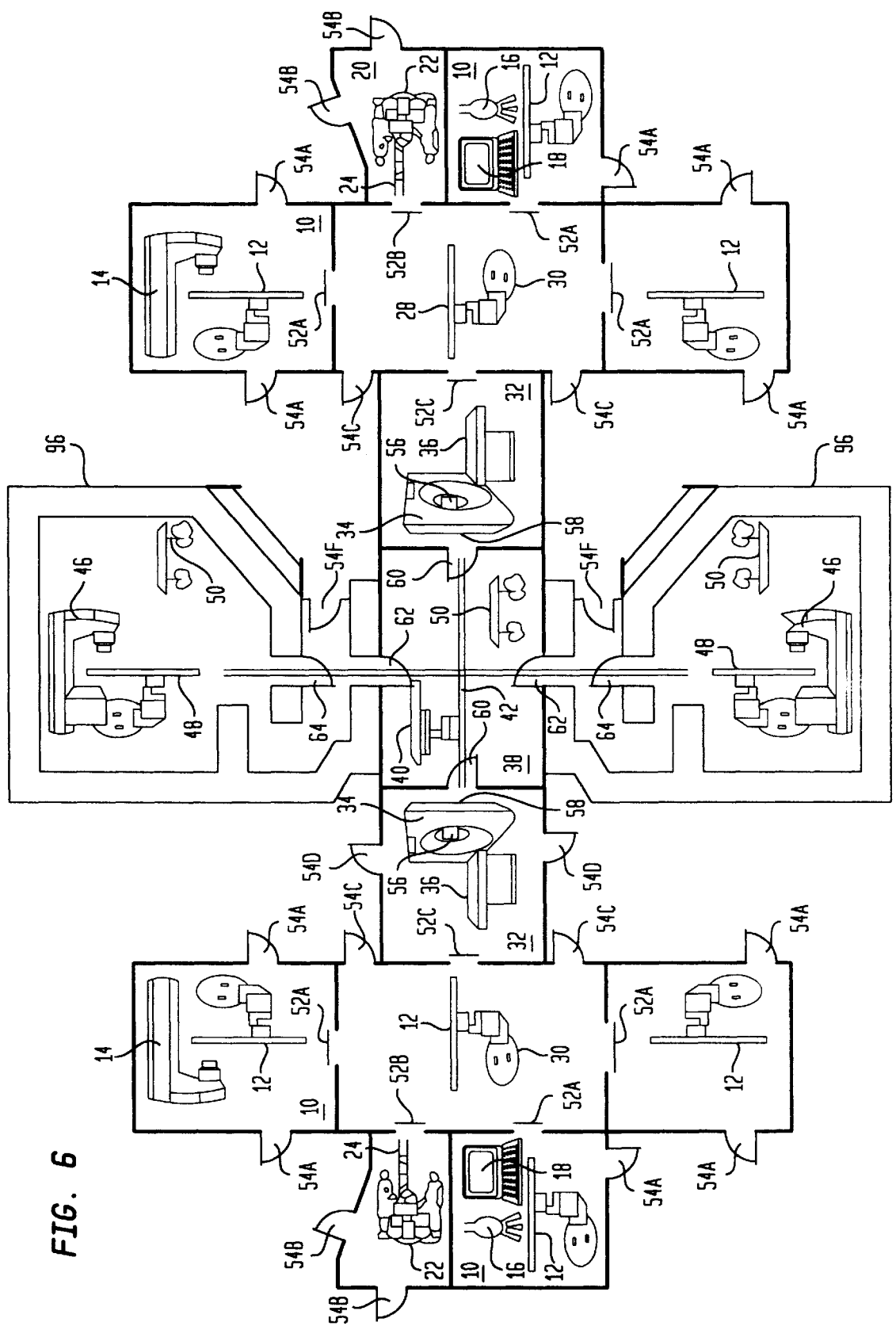
FIG. 6 shows two diagnostic imaging units.

Other Embodiments–FIGS. 4 to 6

Single CT or MRI with an Accelerator–Description–FIG. 4

FIG. 4 is an overall perspective view of the combined medical imaging and radiation therapy with a single CT or MRI and a medical accelerator.

A plurality of preliminary imaging support rooms 10, equipped with preliminary imaging table 12, x-ray unit 14, or ultrasound unit 16, patient transport room 26, with patient transport table 28, on circular rails 30, final imaging room 32, final imaging device with its gantry 34, CT or MRI scanning table 36, sliding doors 52A, 52B, 52C, and entrance and exit doors 54A, 54B, 54C, 54D, 54E, and 54F, all are as in FIG. 1 but in this system patient unloading room 66 is replaced with an accelerator's anteroom 38, which is connected to an accelerator room 44, with radiation protective concrete wall 96, and containing an accelerator 46, an accelerator table 48 and a conveyer table on wheel 50.

In accordance with the invention, preliminary imaging support rooms 10, with x-ray unit 14, or ultrasound unit 16, and surgical room 20 are connected to patient transport room 26, with patient transport table 28. This patient transport table 28 is attached to circular rails 30. Sliding doors 52A, and 52B connect preliminary imaging support rooms 10, and surgical room 20, to patient transport room 26. Sliding door 52C connects patient transport room 26, to final imaging room 32. Entrance and exit doors 54A, 54B, 54C, 54D, 54E, 54F are attached to preliminary imaging support rooms 10, surgical room 20, patient transport room 26, final imaging room 32, accelerator's anteroom 38, and to accelerator room 44. The mobile surgical table 22 is attached to surgical tables' rails 24, on the floor. It leads to patient transport room 26. Gantry's front entrance 56, face CT or MRI scanning table 36, and gantry's back exit 58, faces imaging room's exit door 60, which opens to accelerator's anteroom 38. Rails 42, for patient handling table 40, in accelerators' anteroom 38, leads through a connecting door of accelerators' anteroom and accelerator room 62, to accelerator room 44. It continues through accelerator room's intermediate wall's door 64, to accelerator table 48. Dressing room 94 is attached to accelerator's anteroom 38, through entrance and exit door 54E, in close proximity to an accelerator's entrance and exit door 54F.

Single CT or MRI with an Accelerator–Operation–FIG. 4

The patient setup on preliminary imaging table 12, in preliminary imaging support rooms 10, or on mobile surgical table 22, in surgical room 20, patient's transport to patient transport room 26, and subsequent transfer to CT or MRI scanning table 36, in final imaging room 32, and scanning are done as before. Imaging room's exit door 60, in this instance faces accelerator's anteroom 38. Mobile extension table 40, on rails 42, is brought close to imaging device's patient handling table 36, through imaging room's exit door 60 and gantry's back exit 58, and the patient is transferred to patient handling table 40, in accelerator's ante-room 38. Patient handling table 40, on rails 42, with the patient on it is brought to accelerator room 44, and to accelerator table 48, by moving patient handling table on rail 40, on its rail 42, through connecting door of accelerator's ante-room and accelerator room 62, and accelerator room's intermediate wall's door 64. Flat tabletop insert 68, with patient on it is rolled on top of accelerator table's 48, cradle 70, through its grooves 76. Accelerator 46 is used to administer the radiation therapy to the patient. After treatment, the patient leaves accelerator room 44, through accelerator room's entrance and exit doors 54F. Entry and exit to preliminary imaging support rooms 10, surgical room 20, patient transport room 26, final imaging room 32, accelerator's ante-room 38, and accelerator room 44, is facilitated through their respective entrance and exit doors 54A, 54B, 54C, 54D, 54E and 54F.

The patient remains on flat tabletop insert 68, in an identical position throughout the entire course of patient transport from one table to another and finally to accelerator table 48. After the completion of the radiation therapy, the patient is removed from flat tabletop insert 68. It is then placed on conveyer table on wheel 50, to be transported to preliminary imaging support rooms 10, or to surgical room 20, for its reuse for patient setup and transport as before. The patient is ushered to adjacent dressing rooms 94.

Multiple imaging units–Description–FIG. 5

FIG. 5 shows two diagnostic imaging units of this invention connected to a common patient unloading room.

FIG. 5 shows preliminary imaging support rooms 10, surgical room 20, patient transport room 26, and CT or MRI imaging room 32, with imaging and patient transport systems at each of one side of patient unloading room 66. Multiple CT or MRI is thus connected to patient unloading room 66. Patient unloading room 66 is equipped with multiple patient-handling tables on rail 40, and entrance and exit doors 54E. Preliminary imaging support rooms 10, surgical room 20, patient transport room 26, final imaging room 32, are equipped as in FIG. 1 and 4.

Multiple imaging units–Operation–FIG. 6

After simulated patient setup in preliminary imaging support rooms 10, or after surgery, the patient is transferred on flat table top insert 68, to final imaging room 32, as before for CT or MRI. After CT or MRI flat table top insert 68, with the patient is moved onto patient handling table on rail 40, in patient unloading room 66, through gantry's back exit 58. This table with the patient is then moved on rail 42, in patient unloading room 66 and the patient is unloaded from it. The patient leaves this room through its entrance and exit doors 54E. This combination of multiple imaging units' further increases the patient throughput for combined CT or MRI.

Multiple imaging units with multiple accelerators–Description–FIG. 6

FIG. 6 illustrates two diagnostic imaging units of this invention, one at each of the opposite sides of an accelerator's anteroom and two accelerators, one at each of the other opposite sides of the accelerator's anteroom.

FIG. 6 illustrates preliminary imaging support rooms 10, surgical room 20, patient transport room 26, final imaging room 32, with imaging and patient transport systems at each of one side of accelerator's anteroom 38, and two accelerators 46, one at each of other end of accelerator's anteroom 38. Multiple CT or MRI is thus connected with multiple accelerators 46, through a common accelerator's anteroom 38. Accelerator's anteroom 38 is equipped with multiple patient-handling tables on rail 40. Preliminary imaging support rooms 10, surgical rooms 20, patient transport room 26, final imaging room 32, accelerator's ante-room 38, and accelerator rooms 44, are otherwise equipped as described in FIG. 4.

Multiple imaging units with multiple accelerators–Operation

After simulated patient setup in preliminary imaging support rooms 10, or after surgery, the patient is transferred on flat table top insert 68, to final imaging room 32, as before for CT or MRI. After CT or MRI, flat table top insert 68, with the patient is moved onto patient handling table on rail 40, in patient unloading room 66, through gantry's back exit 58. This table with the patient is then moved on rail 42, in accelerator's anteroom 38. Patient handling table on rail 40, with flat table top insert 68 and the patient is brought to accelerator table 48, by moving patient handling table on rail 40, on its rail 42, through connecting door of accelerator's ante-room and accelerator room 62, and through accelerator room's intermediate wall's door 64. Flat tabletop insert 68, with the patient is rolled over to accelerator table 48, and radiation therapy is given to the previously setup field that was also verified by CT or MRI. After the treatment, the patient is unloaded from accelerator table 48. The patient leave accelerator room 44, through its entrance and exit doors 54F. This combination of multiple imaging units with the accelerators further increases the patient throughput for combined CT or MRI imaging and radiation therapy.

Conclusions, Ramifications, and Scope

Accordingly, it can be seen that, according to the invention, the cost-efficiency of medical imaging is increased with improved patient handling systems for increased patient throughput by imaging devices like CT and MRI. As stated, the patient handling time for CT and MRI imaging in imaging room 32, is significantly reduced. It allows an increased patient throughput by CT and MRI. The greater time consuming initial patient setup and field localization for scanning is done in preliminary imaging support rooms 10. Flat tabletop insert 68, is placed on top of preliminary imaging table 12. The patient rests on flat tabletop insert 68. A preliminary imaging x-ray unit 14, or ultrasound unit 16, is used for the CT and MRI scout's simulation imaging. After the preliminary scout's simulation, flat table top insert 68, with the patient is moved onto patient transport table 28, in patient transport room 26, and then to CT or MRI table 36, in imaging room 32. During this transport of the patient from preliminary imaging table 12, to patient transport table 28, and then to CT or MRI scanning table 36, the patient remains as in previously simulated scout position on flat table top insert 68. The CT or MRI scanning of the previously selected imaging site follows it by scout simulation. This facilitates the completion of the CT or MRI scan in about less than two minutes. The flat tabletop insert 68, with the patient on it is then moved onto patient handling table on rail 40, through gantry's back exit 58 to patient unloading room 66, at a facility intended for medical imaging only. If combined medical imaging and radiation therapy is intended, the patient is transferred to accelerator's anteroom 38.

After the first patient's transfer to CT or MRI scanning table 36, patient transport table 28, is rotated toward next preliminary imaging support room 10, and the next patient is made ready for transport to CT or MRI table 36, as before. After the first patient's scanning is completed and the patient is transferred to patient unloading room 66, or to accelerator's anteroom 38, the next patient is transferred to CT or MRI scanning table 36, for imaging. This process is repeated for rapid successive patient transport to CT or MRI table 36, for the rapid final imaging with a CT or MRI.

The reduced time spent for patient setup on CT or MRI table 36, facilitates an increased patient throughput by the CT or MRI. It increases the patient throughput by a factor of ten or more. The actual CT scanning takes only about two minutes. For combined imaging and radiation therapy, after CT or MRI imaging, the patient is transferred to patient handling table on rail 40, in accelerator's anteroom 38, through gantry's back exit 58, and final imaging room's exit door 60, by moving flat table top insert 68, with the patient on it. Flat tabletop insert 68, is rolled over from one table to the other. The patient remains in CT or MRI treatment field setup position on flat tabletop insert 68. Patient handling table on rail 40, with the patient is then brought to accelerator room 44, and flat table top insert 68, with the patient is rolled over to accelerator table 48. It allows the patient transport to accelerator table 48, with CT or MRI- verified treatment field setup for precise delivery of radiation therapy. This arrangement reduces the time taken for patients' setup on accelerator table 48, for radiation therapy. The time taken for actual delivery of radiation by the accelerator is only about one or two minutes. This facilitates increased patient throughput, by a factor of more than ten times by a single accelerator.

If the patient load for CT or MRI imaging is very high and cannot be met by the increased patient throughput achieved with a single CT or MRI configuration of this invention, the configuration with multiple final imaging devices as in FIG. 5, is used.

If the patient load for combined CT or MRI imaging and radiation therapy is very high and cannot be met by the increased patient throughput achieved with a single CT or MRI combined with a single accelerator, multiple final imaging devices and accelerators, as in FIG. 6, is used.

Although the description above contains many specifics, these should not be construed as limiting the scope of the invention but as merely providing illustrations of some of the presently preferred embodiments of this invention. Various other embodiments and ramifications are possible within its scope. The principle of this invention can be implemented to other medical imaging and radiation therapy systems to reduce its cost. Thus the scope of the invention should be determined by the appended claims and their legal equivalents, rather than by the examples given.

What is claimed is:

1. A system for simulated patient setup for medical imaging, comprising:

a plurality of preliminary imaging support rooms, each said preliminary imaging support room having a preliminary imaging device and a preliminary imaging table;

a patient transport room having a patient transport table, wherein said patient transport room is connected to said plurality of preliminary imaging support rooms;

a final imaging room having a final imaging device with a modified patient handling table; and a patient unloading room having a patient unloading table, wherein said patient unloading room is connected to said final imaging room.

2. The system for simulated patient setup for medical imaging according to claim 1, further comprising a surgical room connected to said patient transfer room.

3. The system for simulated patient setup for medical imaging according to claim 1, further comprising a dressing room connected to said patient unloading room.

4. The system for simulated patient setup for medical imaging according to claim 1, wherein said plurality of preliminary imaging support rooms, said patient transfer room, said final imaging room, and said patient unloading room are connected by means of connecting doors.

5. The system for simulated patient setup for medical imaging according to claim 1, wherein said preliminary imaging device is selected from a x-ray unit or an ultrasound unit with an ultrasound unit computer.

6. The system for simulated patient setup for medical imaging according to claim 1, wherein said final imaging device is selected from a computerized tomographic device or a magnetic resonance imaging device.

7. A system for simulated patient setup for medical imaging and radiation therapy, comprising:

a plurality of preliminary imaging support rooms, each said preliminary imaging support room having a preliminary imaging device and a preliminary imaging table;

a patient transport room having a patient transport table, wherein said patient transport room is connected to said plurality of preliminary imaging support rooms;

a final imaging room having a final imaging device with a modified patient handling table;

an accelerator anteroom connected to said final imaging room; and an accelerator room having radiation protective walls, an accelerator device, an accelerator table, and a conveyer table on wheels, wherein said accelerator room is connected to said accelerator anteroom.

8. The system for simulated patient setup for medical imaging and radiation therapy according to claim 7, wherein said final imaging device is selected from a single computerized tomographic device or a single magnetic resonance imaging device.

9. A system for simulated patient setup for medical imaging, comprising:

a patient unloading room having a patient unloading table, wherein said patient unloading room is connected to two patient imaging systems at opposite ends of said patient unloading room; and each said patient imaging system comprising:

a plurality of preliminary imaging support rooms, each said preliminary imaging support room having a preliminary imaging device and a preliminary imaging table;

a patient transport room having a patient transport table, wherein said patient transport room is connected to said plurality of preliminary imaging support rooms; and a final imaging room having a final imaging device with a modified patient handling table, wherein said final imaging room is connected to said patient transport room and said patient unloading room.

10. The system for simulated patient setup for medical imaging according to claim 9, wherein said final imaging device is selected from a single computerized tomographic device, a single magnetic resonance imaging device, or a combination of a single computerized tomographic device and a single magnetic resonance imaging device.

11. A system for simulated patient setup for medical imaging and radiation therapy, comprising:

a plurality of accelerator rooms, each said accelerator room having radiation protective walls, an accelerator device, an accelerator table, and a conveyer table on wheels;

an accelerator anteroom connected to said plurality of accelerator rooms such that said accelerator rooms are located at opposite ends of said accelerator anteroom and connected to two patient imaging systems located at opposite ends of said accelerator anteroom offset from said accelerator rooms; and each said patient imaging system comprising:

a plurality of preliminary imaging support rooms, each said preliminary imaging support room having a preliminary imaging device and a preliminary imaging table;

a patient transport room having a patient transport table, wherein said patient transport room is connected to said plurality of preliminary imaging support rooms; and a final imaging room having a final imaging device with a modified patient handling table connected to said accelerator anteroom.

12. The system for simulated patient setup for medical imaging according to claim 11, wherein said final imaging device is selected from a single computerized tomographic device, a single magnetic resonance imaging device, or a combination of a single computerized tomographic device and a single magnetic resonance imaging device.

13. A method for transporting a patient for medical imaging with increased patient throughput, comprising the steps of:

a. placing a patient on a table top insert of a preliminary imaging table of a preliminary imaging device located in a preliminary imaging support room;

b. generating preliminary images of the patient with the preliminary imaging device;

c. transporting the patient on said table top insert of the preliminary imaging table onto a patient transport table in a patient transport room;

d. transporting the patient on said table top insert of the patient transport table onto a final imaging table of a final imaging device located in a final imaging room; and e. generating final images of the patient with the final imaging device;

wherein said preliminary imaging room, said patient transport room, and said final imaging room are separate rooms.

14. The method for transporting a patient for medical imaging according to claim 13, further comprising the step of:

f. rolling said table top insert on which the patient is positioned on the final imaging table through a gantry of the final imaging device onto a patient handling table on a rail in a patient unloading room.

15. The method for transporting a patient for medical imaging according to claim 13, wherein said transporting of the patient in said steps (c) and (d) comprise the steps of:

f. rotating and extending the patient transport table in said patient transport room on a rail such that the patient transport table aligns with the preliminary imaging table;

g. rolling said table top insert on which the patient is positioned on the preliminary imaging table onto the patient transport table;

h. rotating and extending the patient transport table in said patient transport room on said rail such that the patient transport table aligns with the final imaging table of the final imaging device in said final imaging room; and i. rolling said table top insert on which the patient is positioned on the patient transport table onto the final imaging table.

16. The method for transporting a patient for medical imaging according to claim 13, further comprising the step of:

f. rolling said table top insert onto a conveyer table after the patient is removed from said table top insert when the final images have been generated in said step (e) and the patient has been transferred to a patient unloading room; and g. transporting said conveyor table with said table top insert positioned thereon from said final imaging room to said preliminary imaging support room such that said table top insert can be used by a second patient.

17. A method for transporting a patient for medical imaging and radiation therapy field setup for increased patient throughput, comprising the steps of:

a. placing a patient on a table top insert of a preliminary imaging device located in a preliminary imaging support room;

b. generating preliminary images of the patient with the preliminary imaging device;

c. transporting the patient on said table top insert to a patient transport table in a patient transport room;

d. transporting the patient on said table top insert to a final imaging device located in a final imaging room;

e. generating final images of the patient with the final imaging device;

f. transporting the patient on said table top insert to an accelerator anteroom;

g. transporting the patient on said table top insert onto an accelerator table of an accelerator device in an accelerator room; and h. treating the patient with the accelerator device in said accelerator room;

wherein said preliminary imaging room, said patient transport room, said final imaging room, said accelerator anteroom, and said accelerator room are separate rooms.

18. The method for transporting a patient for medical imaging and radiation therapy according to claim 17, wherein said transporting of the patient further comprises the steps of:

i. rolling said table top insert on which the patient is positioned when in said final imaging room onto a patient handling table on rails after said final images have been generated;

j. transporting said patient handling table with the patient disposed thereon from said final imaging room to said accelerator anteroom;

k. transporting said patient handling table with the patient disposed thereon from said accelerator anteroom to said accelerator room;

l. rolling said table top insert with the patient disposed thereon from said patient handling table to said accelerator table.

\* \* \* \* \*

UNITED STATES PATENT AND TRADEMARK OFFICE
CERTIFICATE OF CORRECTION

PATENT NO. : 5,842,987
DATED     : December 1, 1998
INVENTOR(S) : Velayudhan Sahadevan It is certified that error appears in the above-identified patent and that said Letters Patent is hereby corrected as shown below:

Column 4, Line 24   delete "a" and insert therefor --and--

Column 7, Line 30   delete "patient handling" and insert therefor --mobile extension--

Column 7, Line 49   delete "patient handling" and insert therefore --mobile extension--

Column 7, Line 50   delete "Patient handling" and insert therefor --Mobile extension--

Signed and Sealed this

Twenty-seventh Day of July, 1999

Attest:

Q. TODD DICKINSON

*Attesting Officer*   *Acting Commissioner of Patents and Trademarks*